US008199835B2

(12) United States Patent
Amini et al.

(10) Patent No.: US 8,199,835 B2
(45) Date of Patent: Jun. 12, 2012

(54) SYSTEMS AND METHODS FOR ADAPTIVE SIGNAL SAMPLING AND SAMPLE QUANTIZATION FOR RESOURCE-CONSTRAINED STREAM PROCESSING

(75) Inventors: Lisa Amini, Yorktown Heights, NY (US); Daby M. Sow, North White Plains, NY (US); Deepak S. Turaga, Elmsford, NY (US); Olivier Verscheure, Hopewell Junction, NY (US)

(73) Assignee: International Business Machines Corporation, Armonk, NY (US)

( * ) Notice: Subject to any disclaimer, the term of this patent is extended or adjusted under 35 U.S.C. 154(b) by 1352 days.

(21) Appl. No.: 11/755,356

(22) Filed: May 30, 2007

(65) Prior Publication Data

US 2008/0298503 A1 Dec. 4, 2008

(51) Int. Cl.
*H04B 14/04* (2006.01)
(52) U.S. Cl. ........ 375/243; 375/278; 375/316; 375/346; 375/355; 375/377
(58) Field of Classification Search .................. 375/316, 375/243, 259, 264, 278, 317, 324, 342, 346, 375/377, 355
See application file for complete search history.

(56) References Cited

U.S. PATENT DOCUMENTS

| | | | |
|---|---|---|---|
| 6,597,811 B1 * | 7/2003 | Batkilim et al. | 382/232 |
| 6,947,886 B2 * | 9/2005 | Rose et al. | 704/200.1 |
| 7,403,875 B2 * | 7/2008 | Vogel et al. | 702/189 |
| 2006/0052717 A1 * | 3/2006 | Mugler et al. | 600/509 |
| 2007/0150525 A1 * | 6/2007 | Idicula et al. | 707/203 |

OTHER PUBLICATIONS

Derpich et al. "Quantization and sampling of not necessarily band-limited signals", May 2006 , ICASSP, pp. 396-399.*
Bohs et al "Real-time adaptive sampling with the fan algorithm" Nov. 1988., Medical and Biological Engineering and Computing, pp. 565-573.*
M.S. Derpich et al., "Quantization and Sampling of Not Necessarily Band-Limited Signals", In IEEE International Conference on Acoustics, Speech and Signal Processing, 2006.
J. Katzenelson, "On Errors Introduced by Combined Sampling and Quantization", In IRE Transactions on Automatic Control, vol. AC7, pp. 58-68, 1962.
R. Crinon et al., "Vector Quantization With Adaptive Sampling (VQAS)", In IEEE International Symposium on Circuits and Systems, No. 4, pp. 3126-3129, 1990.
D.A. DiPersio et al., "Evaluation of the FAN Method of Adaptive Sampling on Human Electrocardiograms", In Medical Biological Engineering Computing, pp. 401-410, 1985.
A. Ruha et al., "A Real-Time Microprocessor QRS Detector System with a 1-ms Timing Accuracy for the measurement of Ambulatory HRV", In IEEE Transactions on Biomedical Engineering, vol. 44, pp. 159-167, 1997.
L.W. Gardenhire, "Redundancy Reduction the Key to Adaptive Telemetry", In Conference National Telemetry, pp. 1-16, 1964.

* cited by examiner

*Primary Examiner* — Chieh M Fan
*Assistant Examiner* — Sophia Vlahos
(74) *Attorney, Agent, or Firm* — Cantor Colburn LLP; William J. Stock

(57) ABSTRACT

Systems and methods for adaptive signal sampling and sample quantization for resource-constrained stream processing. Exemplary embodiments include a signal sampling and signal quantization method for a data stream from a ECG sensor into a pervasive device, the method including adaptively sampling the data stream, compressing data samples from the data stream, reducing the number of samples via quantization, defining a utility function for signal reconstruction, and formulating optimization on the reconstructed signal that is jointly sampled and quantized.

3 Claims, 4 Drawing Sheets

SYSTEMS AND METHODS FOR ADAPTIVE SIGNAL SAMPLING AND SAMPLE QUANTIZATION FOR RESOURCE-CONSTRAINED STREAM PROCESSING

TRADEMARKS

IBM® is a registered trademark of International Business Machines Corporation, Armonk, N.Y. U.S.A. Other names used herein may be registered trademarks, trademarks or product names of International Business Machines Corporation or other companies.

BACKGROUND OF THE INVENTION

1. Field of the Invention

This invention relates to signal sampling, and particularly to systems and methods for adaptive signal sampling and sample quantization for resource-constrained stream processing.

2. Description of Background

Several emerging applications including network traffic monitoring, financial data feeds, telemetry applications, medical data (e.g., ECGs), etc., contain streaming data arriving at high rates. Often, the system cannot either support the data rate or the computational complexity required for processing these streams. For example, a typical electrocardiogram-monitoring device generates massive volumes of digital data. Depending on the intended application for the data, the sampling rate ranges from 125 to 500 Hz. Each data sample is digitized to a 8 to 12 bit binary number. Even at the lowest sampling rate in the range and assuming just one sensor that generates 8-bit data, we would accumulate ECG data at a rate of 7.5 KB per minute or 450 KB per hour.

Traditional lossy techniques for stream adaptation to meet resource constraints involve reducing the rate of the original streams using either quantization, or stream sub-sampling (and sometimes both). Quantization involves mapping signal x[k] onto a coarser version x'[k] that requires fewer bits to represent. Hence, if the original signal requires $b_u$ bits per sample, quantization results in a signal with $b_q < b_u$ bits per sample, thereby reducing the average data rate of the stream by a factor $b_u/b_q$. There are several optimal (in terms of specific metrics) scalar and vector quantization schemes that may be designed specific to the application and data characteristics.

Uniform subsampling involves discarding samples of the data (evenly) to reduce the data rate. Hence in order to reduce the data rate by a factor $\alpha$ ($\alpha > 1$) these schemes retain only one out of every $\alpha$ samples (spaced evenly), thereby resulting in stream $x \sim [\alpha k]$. Often some filtering (low-pass) is applied to the signal prior to subsampling to avoid aliasing and also to tune the subsampling to the requirements of the application.

Hence, there is need for algorithms and methods that can efficiently adapt the streams to match the underlying system resource (rate and complexity) constraints while minimizing the impact of this adaptation on any results that need to be derived from these streams. As such, streams that perform both quantization and uniform subsampling jointly to match the underlying system resource constraints are needed.

SUMMARY OF THE INVENTION

Exemplary embodiments include a signal sampling and signal quantization method for a data stream, the method consisting of sampling the data stream of an original signal to identify samples of interest non-uniformly in time, the sampling of the data stream being performed by a non-uniform sampling algorithm, applying quantization to reduce a rate of the data stream, wherein the sampling of the data stream and the quantization of the data stream is performed jointly to tolerate a plurality of levels of quantization noise and to accommodate a plurality of samples of interest, applying a utility function to reconstruct a signal from the jointly sampled and quantized data stream and formulating and solving an optimization to maximize the utility function under available constraints.

Further embodiments include a signal sampling and signal quantization method for a data stream from a ECG sensor into a pervasive device, the method including sampling the data stream of an original signal to identify samples of interest non-uniformly in time, the sampling of the data stream being performed by a FAN algorithm, retaining the identified samples through a bit location vector containing one bit per sample of the original signal, assigning a value "1" to retained samples and a value "0" to discarded samples, possibly compressing the bit location vector using entropy coding techniques (that could include arithmetic coding or run-length coding), applying quantization to reduce a rate of the data stream, wherein the sampling of the data stream and the quantization of the data stream of performed jointly to tolerate a plurality of levels of quantization noise and to accommodate a plurality of samples of interest, applying a utility function to reconstruct a signal from the jointly sampled and quantized data stream, the utility function being defined by:

$$U(x[k], x_r[k]) = -100 * \sqrt{\frac{\sum_{j=1}^{N}(x[j] - x_r[j])^2}{\sum_{j=1}^{N} x[j]^2}}$$

wherein x[k] is the original signal, $x_r$[k] is the reconstructed signal, k is a sample location, and N is the total number of samples and formulating an optimization on the reconstructed signal from the jointly sampled and quantized data stream, wherein the reconstructed signal is determined from the quantized and sampled signal by inverse quantization and linear interpolation to determine discarded samples.

System and computer program products corresponding to the above-summarized methods are also described and claimed herein.

Additional features and advantages are realized through the techniques of the present invention. Other embodiments and aspects of the invention are described in detail herein and are considered a part of the claimed invention. For a better understanding of the invention with advantages and features, refer to the description and to the drawings.

TECHNICAL EFFECTS

As a result of the summarized invention, technically we have achieved a solution in which systems and methods include adaptive signal sampling and sample quantization for resource-constrained stream processing. As such, both joint quantization and non-uniform sampling are jointly performed on data streams.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

The detailed description explains the preferred embodiments of the invention, together with advantages and features, by way of example with reference to the drawings.

DETAILED DESCRIPTION OF THE INVENTION

Exemplary embodiments include systems and methods that combine irregular signal sampling together with sample quantization to reduce the amount of data to be transmitted (and/or processed) to (by) a backend-processing unit. Extraction of the information (data samples) most relevant to the application processing the incoming data in the backend unit can be implemented. The joint sampling and quantization method requires maximizing a user-defined utility metric under given system resource constraints such as maximum transmission rate or computational complexity in the backend unit. In accordance with exemplary embodiments, the optimization problem for the utility defined as the percentage root-mean-square difference between the original signal and its reconstructed (inverse quantization and linear interpolation) version is solved.

Figure 1:
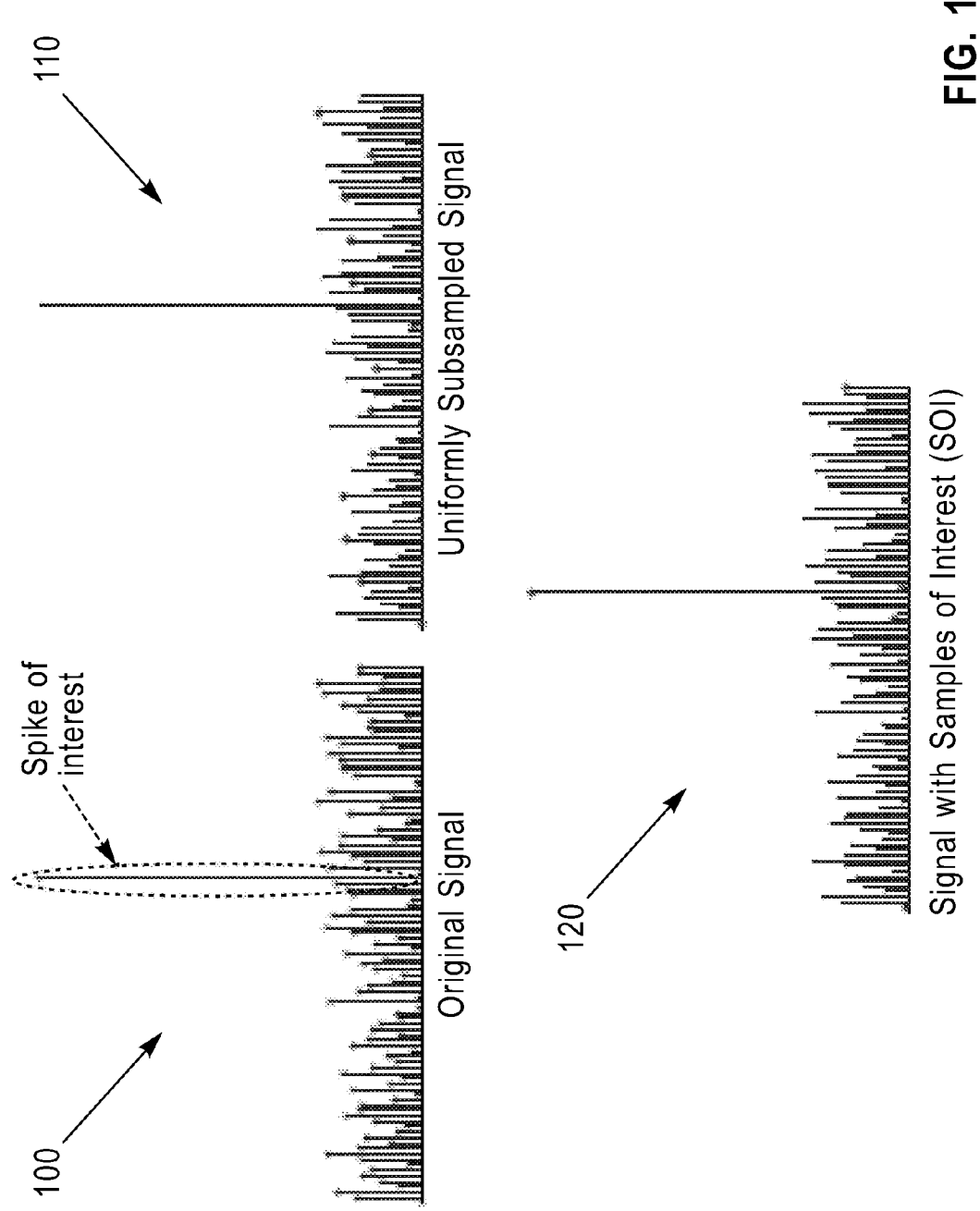
FIG. 1 illustrates signal sampling in accordance with exemplary embodiments.

While uniform sub-sampling can reduce the stream rate appropriately it does not guarantee the retention of all samples of interest (features), especially when the frequency characteristics of the stream are not well behaved (e.g. streams that are not band-limited). This characteristic can have a severe impact on any applications that depend on observing specific (often rapid) patterns in the stream. FIG. 1 illustrates signal sampling in accordance with exemplary embodiments. Sample 100 illustrates an original single. Sample 110 illustrates the original single sampled implementing sub-sampling. Sample 120 illustrates the original signal sampled by sampled of interest. In general, the signal of FIG. 1 illustrates an application that includes the detection of a sharp sudden spike.

Referring still to FIG. 1, sub-sampling 110 the signal by a factor 8 leads to the spike not being observed, thereby severely impacting any results the application may require. As mentioned above, and discussed further below the data stream can be adaptively sampled. However, using sampling of interest 120, five samples results in data reduction as well as the retention of the samples of interest (corresponding to the spike). Therefore, the stream data can be reduced by retaining only the relevant samples of interest (SOI) while discarding other samples, instead of uniformly sub-sampling the stream. As a result, however, retaining only the samples of interest leads to a stream with samples spaced non-uniformly in time. This process takes the signal x[k] and converts it to $x[k_1]$ where $k_1$ corresponds to the location of the retained sample. In one example, information about the location of the retained samples may be encoded using a bit-location vector. This vector contains 1 bit per sample of the original signal, and takes value 1 corresponding to sample being retained and value 0 corresponding to sample being discarded. The vector may further be compressed, (using run-length coding or arithmetic coding) to a rate $r_{by} \leq 1$ bits per sample. $N_{SoI}$ out of N samples can be retained, and the rate of the resultant signal is reduced by a factor:

$$\frac{N_{SOI}(b_u + 1)}{Nb_u}$$

Several different linear and non-linear schemes may be designed to retain samples-of-interest in the stream. As discussed above, the data stream can be adaptively sampled. In an exemplary implementation, a FAN algorithm can be implemented to sample the data stream. It is appreciated that for some signals it may not be enough to retain the samples of interest to meet resource constraints (when NsoI→N). Therefore, in an exemplary implementation, a quantization scheme can also be used in addition to the non-uniform sampling to further reduce the rate of the stream. With these two schemes combined the resulting rate of the stream may be further reduced to $N_{SOI}(B_q+1)/Nb_u$.

Different types of streams and application can tolerate different levels of quantization noise and require different numbers of samples of interest. Hence the design of the quantization and the non-uniform sampling scheme can be performed jointly. In one embodiment, the quantization can be represented as: Q:x[k]→x'[k] and the non-uniform sampling as S:x[k]→x[$k_i$]. As a result, the quantization followed by sub-sampling can be represented as: S(Q(x[k])) and sub-sampling followed by quantization as Q(S(x[k])). The corresponding rate reduction factors can then be:

$$\frac{N_{SOI}^{S(Q)}(b_q^{S(Q)} + 1)}{Nb_u}$$

$$\frac{N_{SOI}^{Q(S)}(b_q^{Q(S)} + 1)}{Nb_u}$$

In addition, the utility that the application derives from the quantized and sampled signal is defined as U( ). Furthermore, if the system, resource constraint requires a rate reduction factor of $r_{com}$, then the cases can be designed jointly by resolving the constrained optimization;

$$\{Q_{opt}, S_{opt}\} = \mathrm{argmax}_{\{Q,S\}}[U(x[k], Q(S(x[k])))]$$

subject to $$\frac{N_{SOI}^{Q(S)}(b_q^{Q(S)} + 1)}{Nb_u} \leq r_{con}$$

and $$\{S_{opt}, Q_{opt}\} = \mathrm{argmax}_{\{S,Q\}}[U(x[k], S(Q(x[k])))]$$

subject to

-continued $$\frac{N_{SOI}^{S(Q)}(b_q^{S(Q)} + 1)}{Nb_u} \leq r_{con}$$

In general, the quantizer Q requires determining the number of quantization levels and the placement of the reconstruction levels, while designing the non-uniform sampling S strategy requires determining the algorithm and parameters to find the number of samples-of-interest (SOI) and to locate them. Any optimization needs to consider the tradeoff between the parameters for Q and S as they operate under one combined constraint. Finally, if the order of the quantization and non-uniform sampling also needs to be determined, the optimal utilities in the two cases can be compared to one another in order to determine the best order.

In an exemplary embodiment a given compression ratio under strict computational complexity constraints is targeted. For example, electrocardiogram (ECG) signals received by a low-power device connected to a backend unit via a low-bandwidth channel are considered. The low-power device must compress the incoming ECG signal under strict complexity (low-power device) and rate (low-bandwidth channel) constraints before streaming it to the backend unit for storage and processing. In accordance with exemplary embodiments, a method implements adaptive sampling before quantization (i.e. S before Q).

When storing or transmitting over low-bandwidth channels, an ECG recording that spans more than a few minutes, some form of data compression is highly desirable. Recording over quite long periods, as much as 24 hours, may be needed when a patient has complained of irregular heart rhythms. Doctors may wish to build a database of ECG recordings for their patients so that two ECG traces taken on different dates may be compared.

Figure 2:
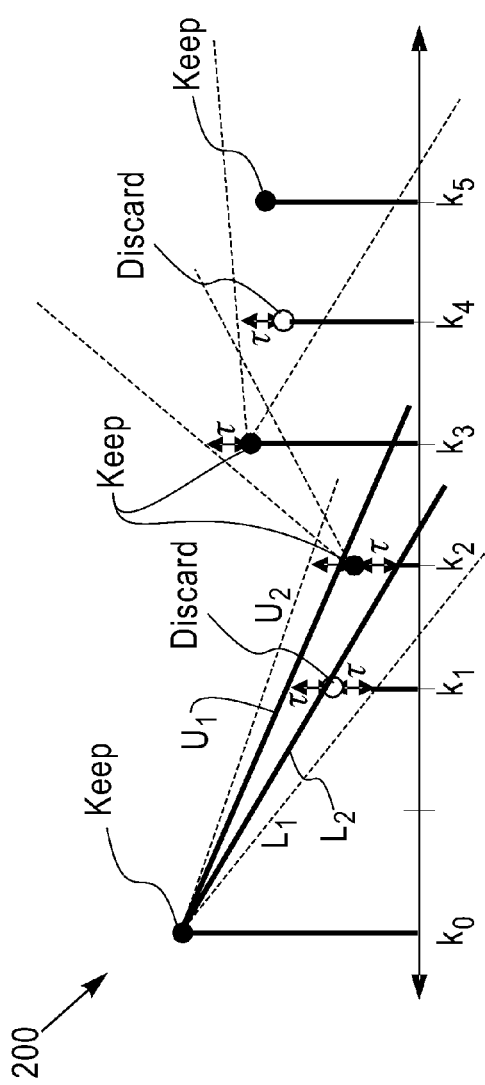
FIG. 2 illustrates a sampling graph of a linear interpolation scheme for non-uniform sampling in accordance with exemplary embodiments.

Therefore, to implement adaptive sampling a standard sampling technique such as FAN can be used for ECG signals. FAN extracts significant signal samples to represent the signal. The basic idea is to identify signal segments where a straight line serves as a close approximation, and discard all but the terminal points along this line. More precisely, the FAN algorithm replaces the original waveform with straight-line segments such that none of the original points lies further from the line segment than some predetermined maximum deviation τ. FIG. 2 illustrates a sampling graph 200 of a linear interpolation scheme for non-uniform sampling in accordance with exemplary embodiments. The first point $x(k_0)$ is accepted as non-redundant (permanent) sample. Two slopes $(L_1, U_1)$ are drawn between the initial point $x(k_0)$ and the next sample plus a specified threshold $\{x(k_1)-\tau, x(k_1)+\tau\}$. The third sample point $x(k_2)$ falls within the area bounded by the two slopes. New slopes $\{L_2, U_2\}$ are calculated between the sample at time $k_0$ and the 3 third sample point plus +,−τ. The two pairs of slopes are compared and the most restrictive are retained: $U_2$=min $(U_2, U_1)$ and $L_2$=max $(L_1, L_2)$. In general, the process is repeated, comparing future sample values to the most restrictive lines. For example, sample at time $k_1$ falls outside the range and is thus discarded; sample at time $k_2$ is accepted as a permanent sample and the procedure above is repeated at future intervals. Upon signal reconstruction, the permanent samples are connected with straight lines.

The parameter τ is an adaptive threshold that determines the quality of the approximation. If the threshold is large, more samples are discarded, and similarly if the threshold is small, that is, fewer samples are discarded.

It is thus appreciated that by implementing the FAN algorithm, computations remain light and perform well in practice. In an exemplary embodiment, the data samples are jointly quantized together with adaptive sampling to further compress the signal.

In order to quantize the samples, a standard mean squared error (MSE) quantizer is derived optionally for a known underlying probability density function. The locations of the reconstruction levels are known for an MSE quantizer. Therefore, the number of reconstruction levels $L=S^{b_q}$ is the only free parameter that may be used to modify the quantizer performance.

In an exemplary embodiment, for joint sampling and quantization, the utility function U( ) is defined, as discussed above, to gauge the reconstruction quality of the compressed signal. A common metric for ECG signals is the percentage root-mean-square difference (PRD) between the original signal and its reconstructed (inverse quantization and linear interpolation) version.

The reconstructed signal $x_r[k]$ is determined from the quantized and sampled signal $S(Q(x[k]))$ by inverse quantization and linear interpolation to determine the discarded samples, (i.e., let $x_r[k]=H(S(Q(x[k])))$).

Therefore, the utility function is defined as:

$$U(x[k], x_r[k]) = -100 * \sqrt{\frac{\sum_{j=1}^{N}(x[j] - x_r[j])^2}{\sum_{j=1}^{N} x[j]^2}}$$

Finally, the joint sampling and quantization problem may be written as the following quantization problem under rate constraint $\tau_{con}$:

$$\{\tau_{opt}, L_{opt}\} = \text{argmax}_{\{\tau,L\}}[U(x[k], x_r[k])]$$

subject to $$\frac{N_{SOI}^{S(Q)}(b_q^{S(Q)} + 1)}{Nb_u} \leq r_{con}$$

This two dimensional problem is solved using standard optimization techniques. In this optimization, the number of levels in the quantizer is determined (and not their position, which can be determined for a different number of bits). Therefore, in one exemplary implementation, the search complexity for this optimization is $O(|\Omega_\tau|\times|\Omega_L|)$, where $\Omega_\tau$ is the set of possible values for τ, $\Omega_L$ is the set of possible values for L and | | is the cardinality operator. $O(|\Omega_\tau|\times|\Omega_L|)$ is therefore a constant factor that multiplies the complexity of the FAN algorithm (thereby linearly increasing the complexity). As such, it is also the worst cases metric as it assumes no apriori knowledge of the underlying ECG signal. Due to the periodic nature of the ECG signal, the assumed design of the answer is likely to change slowly with time (across consecutive windows of N samples each), and hence the complexity can be distributed over several windows. This process may be done by either solving the optimization once every W windows, thereby reducing the overhead complexity to $O((|\Omega_\tau|\times|\Omega_L|)/W)$ or by reducing the space of possible search values, i.e., the number of elements in each set (allowing only for small variations in the previously designed values).

Additional improvement in performance may be obtained by designing the complete quantizer (including the placement of levels) dynamically. This approach introduces increased complexity. In a worst case, making no assumptions regarding the ECG signal, a standard k-means based implementation of quantizer design has complexity $O(N^L)$. The cost of increased complexity can be distributed over several windows (due to the nature of the ECG signal) as previously discussed with respect to low complexity solutions.

Figure 3:
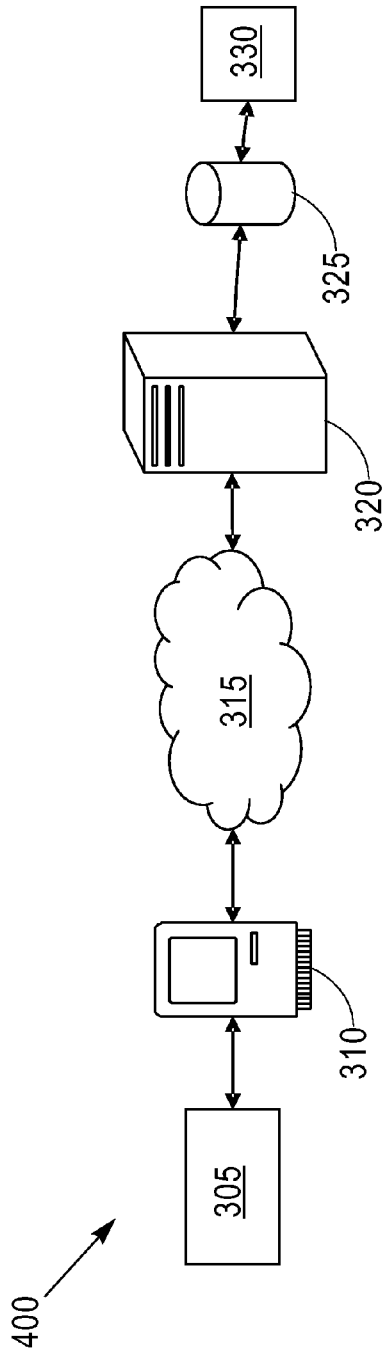
FIG. 3 illustrates an exemplary adaptive signal sampling and quantization system.

FIG. 3 illustrates an exemplary adaptive signal sampling and quantization system 300. In general, ECG data can be collected by sensor equipment 305 that can be coupled to a personal pervasive device 310 as a relay to a remote server 320. In general, the pervasive device 310 can be coupled to the remote server 320 via a network 315. The remote server 320 can include a storage medium 325, which can in turn store a process for implementing the methods described herein. It is therefore appreciated that the system 300 is a three-tier architecture (sensor equipment 305→pervasive device 310→remote server 320). In an exemplary implementation the sensor equipment 305 can transmit the data via Bluetooth to the pervasive device 310. As such, it is further appreciated that the pervasive device 310 is resource-constrained, thereby having limited transmission capacity and limited computational power. As such, the methods described herein can be implemented.

Figure 4:
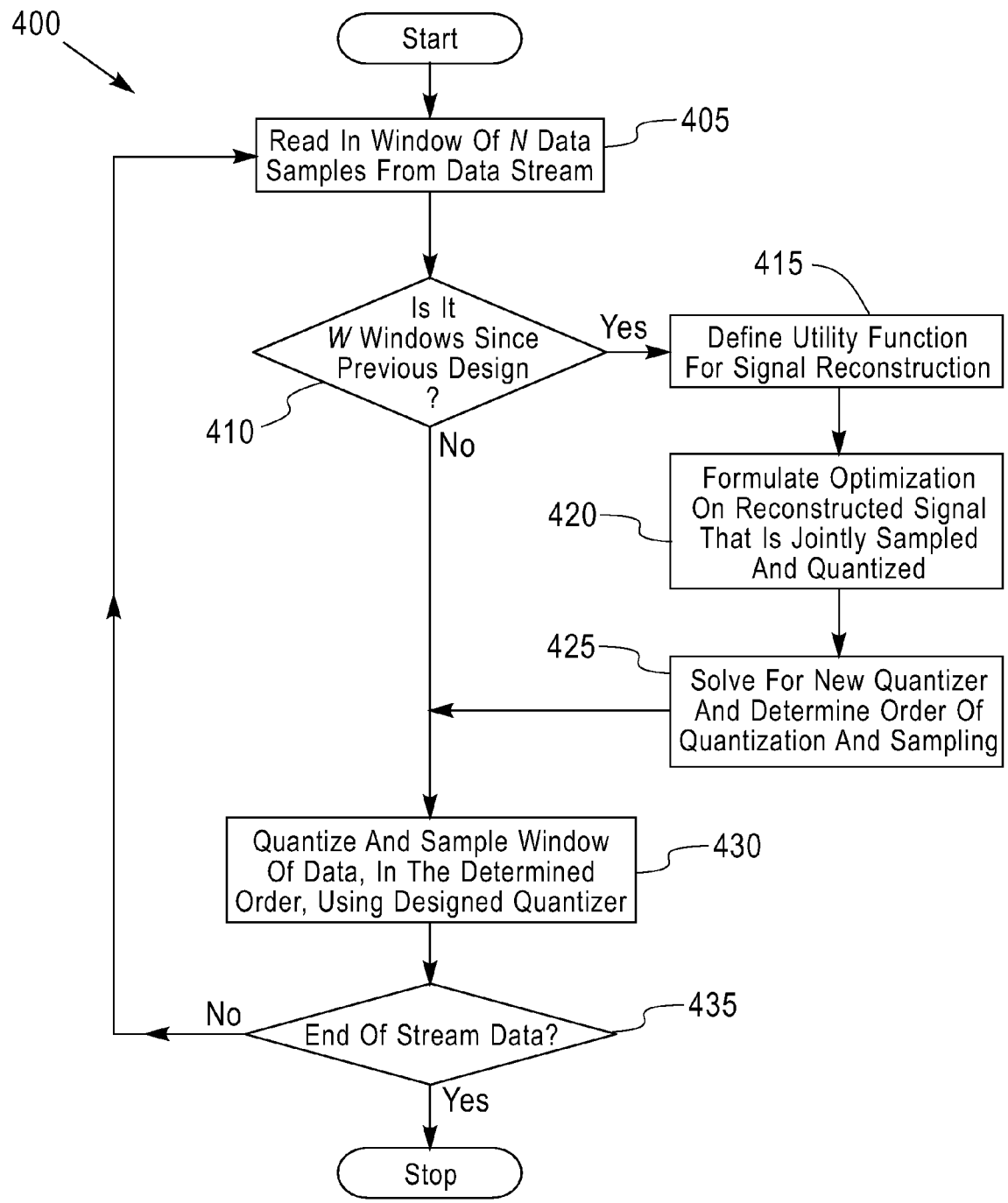
FIG. 4 illustrates a flow chart for a method of adaptive signal sampling and quantization in accordance with exemplary embodiments.

FIG. 4 illustrates a flow chart for a method of adaptive signal sampling and quantization in accordance with exemplary embodiments as described above. At step 405, a window of N data samples is read from a data stream. At step 410, it is determined whether it has been W windows since a previous design. If it has been w windows at step 410, then a utility function for signal reconstruction is defined. At step 415. At step 420, optimization on a reconstructed signal that is jointly sampled and quantized is performed. At step 425, the method 400 solves for a new quantizer and a new order of quantization and sampling is determined. At step 430 the window of data is quantized and sampled, in the determined order using the designed quantizer. Referring back to step 410, if it is determined that it has not been W windows since the previous design, then at step 430 the window of data is quantized and sampled, in the determined order using the designed quantizer. At step 435, the method 400 determines if it is the end of the stream data. If it is not the end of the stream data then step 405 is repeated. If it is the end of the stream data, then the method 400 stops.

EXAMPLE

Figure 5:
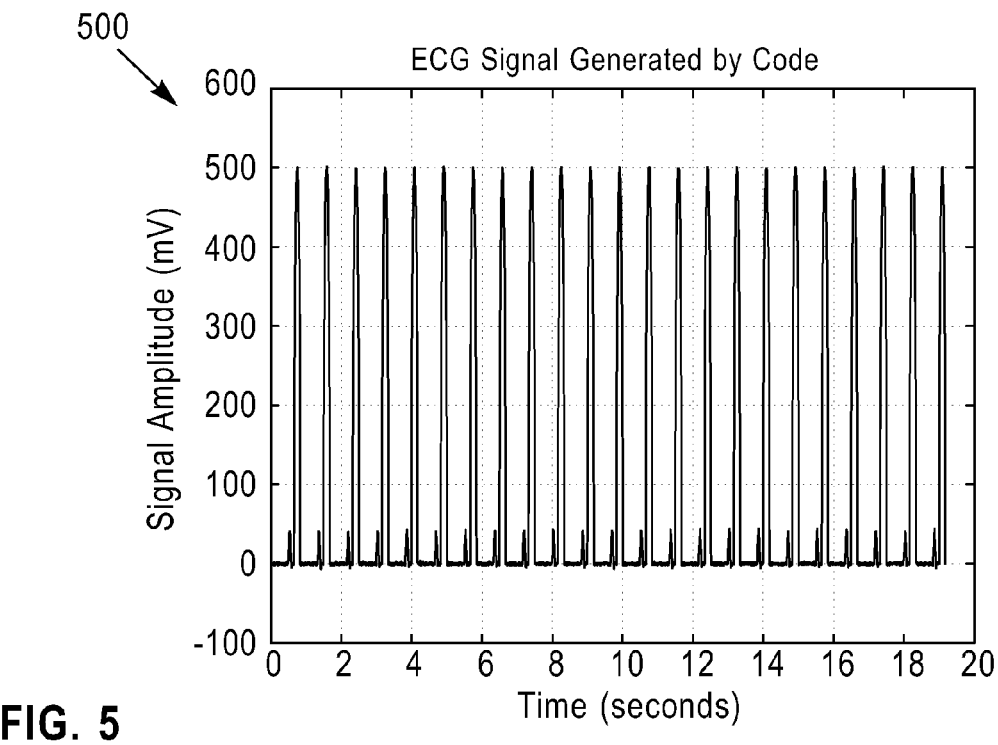
FIG. 5 illustrates one example of a generated ECG signal.

The methods described above are applied to noisy synthetic ECG signals. The ECG signals are generated by ECGwaveGen from the Physio Toolkit (open source software for biomedical science and engineering). ECGwaveGen generates a synthesized ECG signal with user-settable heart rate, signal duration, sampling frequency, QRS amplitude and duration, and T-Wave amplitude; it uses QRSpulse to create premature beats followed by compensatory pauses. The algorithm is based in part on an artificial ECG signal based on the standard test waveforms specified in ANSI/AAMI EC 13: 1992 (American National Standard: Cardiac Monitors, Heart Rate Meters, and Alarms), available from AAMI. The ECG signal is degraded by zero-mean additive white Gaussian noise (AWGN) of a given variance $\sigma^2$. The generated signal is illustrated in FIG. 5.

Figure 6:
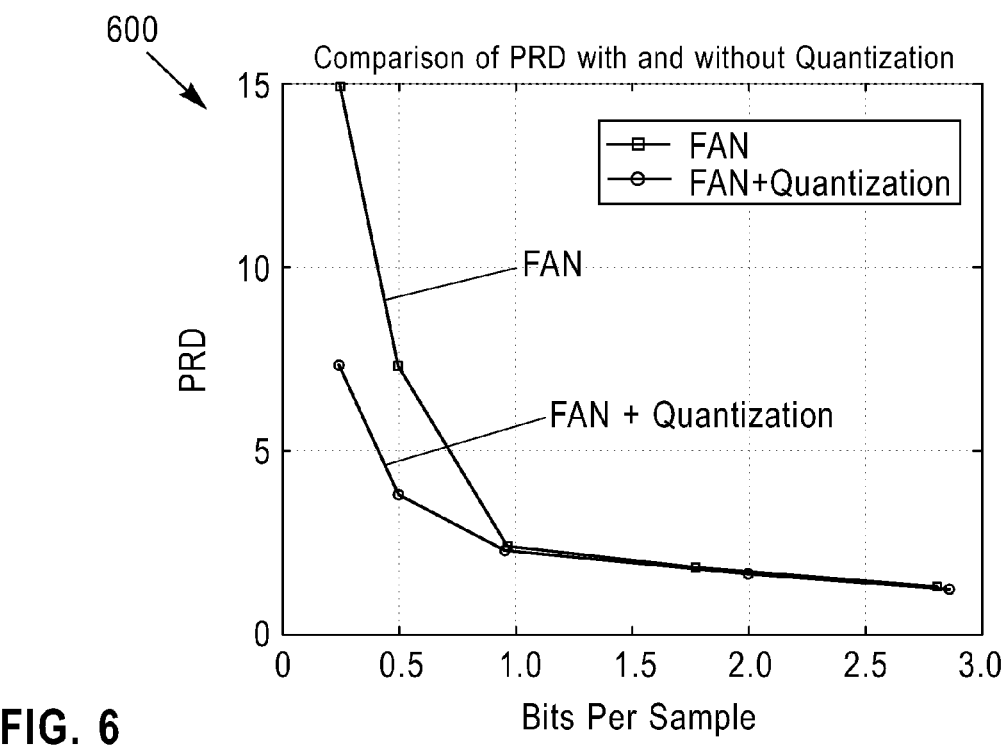
FIG. 6 illustrates one example of the generated ECG signal as generated in FIG. 5 with an applied FAN algorithm and an applied FAN plus quantization algorithm in accordance with exemplary embodiments.

FIG. 6 demonstrates the validity of the present invention applied to noisy ECG signals with $\sigma^2=1$. Two algorithms are compared: FAN only and FAN+quantization. The pro-posed method clearly outperforms the FAN strategy without increasing significantly the computational complexity.

The capabilities of the present invention can be implemented in software, firmware, hardware or some combination thereof.

As one example, one or more aspects of the present invention can be included in an article of manufacture (e.g., one or more computer program products) having, for instance, computer usable media. The media has embodied therein, for instance, computer readable program code means for providing and facilitating the capabilities of the present invention. The article of manufacture can be included as a part of a computer system or sold separately.

Additionally, at least one program storage device readable by a machine, tangibly embodying at least one program of instructions executable by the machine to perform the capabilities of the present invention can be provided.

The flow diagrams depicted herein are just examples. There may be many variations to these diagrams or the steps (or operations) described therein without departing from the spirit of the invention. For instance, the steps may be performed in a differing order, or steps may be added, deleted or modified. All of these variations are considered a part of the claimed invention.

While the preferred embodiment to the invention has been described, it will be understood that those skilled in the art, both now and in the future, may make various improvements and enhancements which fall within the scope of the claims which follow. These claims should be construed to maintain the proper protection for the invention first described.

What is claimed is:

1. A signal sampling and signal quantization method for a data stream, the method consisting of:
    sampling, in a processor, the data stream of an original signal to identify samples of interest non-uniformly in time, the sampling of the data stream being performed by a non-uniform sampling algorithm, wherein the non-uniform sampling algorithm is a FAN algorithm that replaces the original signal with straight-line segments whereby original points of the original signal lie within the line segments at a distance less than a predetermined maximum deviation;
    applying, in the processor, quantization to reduce a rate of the data stream, wherein the sampling of the data stream and the quantization of the data stream is performed jointly to tolerate a plurality of levels of quantization noise and to accommodate a plurality of samples of interest;
    applying, in the processor, a utility function to estimate a quality of a reconstructed signal from the jointly sampled and quantized data stream; and
    formulating and solving, in the processor, an optimization to maximize the utility function under available constraints,
    retaining, in the processor, the identified samples through a bit location vector containing one bit per sample of the original signal;
    assigning, in the processor, a value "1" to retained samples and a value "0" to discarded samples; and
    compressing the bit location vector using entropy coding techniques that include run-length coding or arithmetic coding,
    wherein the quantization is derived from mean squared error having a underlying probability density function,
    wherein the utility function is a percentage root-mean-square difference between the original signal and the reconstructed signal, wherein the reconstructed signal is determined from the quantized and sampled signal by inverse quantization and linear interpolation to determine discarded samples.

2. A signal sampling and signal quantization method for a data stream from an ECG sensor into a pervasive device, the method comprising:

sampling, in a processor, the data stream of an original signal to identify samples of interest non-uniformly in time, the sampling of the data stream being performed by a FAN algorithm;

retaining, in the processor, the identified samples through a bit location vector containing one bit per sample of the original signal;

assigning, in the processor, a value "1" to retained samples and a value "0" to discarded samples;

compressing, in the processor, the bit location vector using entropy coding techniques that include run-length coding or arithmetic coding;

applying, in the processor, quantization to reduce a rate of the data stream, wherein the sampling of the data stream and the quantization of the data stream is performed jointly to tolerate a plurality of levels of quantization noise and to accommodate a plurality of samples of interest;

applying, in the processor, a utility function to estimate a quality of a reconstructed signal from the jointly sampled and quantized data stream, the utility function being defined by:

$$U(x[k], x_r[k]) = -100 * \sqrt{\frac{\sum_{j=1}^{N}(x[j] - x_r[j])^2}{\sum_{j=1}^{N} x[j]^2}}$$

wherein x[k] is the original signal, $x_r$[k] is the reconstructed signal, k is a sample location, and N is the total number of samples; and formulating, in the processor, an optimization on the reconstructed signal from the jointly sampled and quantized data stream, wherein the reconstructed signal is determined from the quantized and sampled signal by inverse quantization and linear interpolation to determine discarded samples.

3. The method as claimed in claim 2 wherein the optimization is performed once every predetermined number of windows of a plurality of samples in each window.

* * * * *